(12) United States Patent
Shinno et al.

(10) Patent No.: US 8,287,704 B2
(45) Date of Patent: Oct. 16, 2012

(54) LIQUID SAMPLE MEASUREMENT METHOD AND APPARATUS

(75) Inventors: Teppei Shinno, Ehime (JP); Yoshifumi Takahara, Ehime (JP)

(73) Assignee: Panasonic Corporation, Osaka (JP)

( * ) Notice: Subject to any disclaimer, the term of this patent is extended or adjusted under 35 U.S.C. 154(b) by 0 days.

(21) Appl. No.: 13/349,729

(22) Filed: Jan. 13, 2012

(65) Prior Publication Data

US 2012/0103806 A1    May 3, 2012

Related U.S. Application Data

(62) Division of application No. 12/307,340, filed as application No. PCT/JP2007/063336 on Jul. 4, 2007.

(30) Foreign Application Priority Data

Jul. 5, 2006  (JP) ................................. 2006-186033

(51) Int. Cl.
*G01N 27/27* (2006.01)
(52) U.S. Cl. ................. 204/406; 205/777.5; 204/403.02
(58) Field of Classification Search .......... 204/403.01–403.15, 406; 205/777.5, 205/778, 792; 600/345–348
See application file for complete search history.

(56) References Cited

U.S. PATENT DOCUMENTS

| | | | |
|---|---|---|---|
| 4,303,887 A | 12/1981 | Hill et al. | |
| 4,713,165 A | 12/1987 | Conover et al. | |
| 5,405,511 A | 4/1995 | White et al. | |
| 5,695,623 A | 12/1997 | Michel et al. | |
| 6,780,296 B1 | 8/2004 | Bhullar et al. | |
| 2003/0159945 A1* | 8/2003 | Miyazaki et al. | 205/777.5 |
| 2004/0238357 A1 | 12/2004 | Bhullar et al. | |
| 2005/0019219 A1 | 1/2005 | Oshiman et al. | |
| 2007/0045126 A1 | 3/2007 | Beer et al. | |
| 2007/0173710 A1 | 7/2007 | Petisce et al. | |

FOREIGN PATENT DOCUMENTS

| | | |
|---|---|---|
| JP | 8-503304 | 4/1996 |
| JP | 11-023512 | 1/1999 |
| JP | 11-23512 | 1/1999 |
| JP | 2001-235444 | 8/2001 |
| JP | 2003-42995 | 2/2003 |
| JP | 2005-221279 | 8/2005 |
| WO | 94/29704 | 12/1994 |
| WO | 03/062812 | 7/2003 |

OTHER PUBLICATIONS

International Search Report issued Oct. 9, 2007 in International (PCT) Application No. PCT/JP2007/063336.
Written Opinion of the ISA issued Oct. 9, 2007 in International (PCT) Application No. PCT/JP2007/063336.
Extended European Search Report issued Apr. 20, 2012 in corresponding European Application No. 07768106.2.

* cited by examiner

*Primary Examiner* — Kaj K Olsen
*Assistant Examiner* — Kourtney R Carlson
(74) *Attorney, Agent, or Firm* — Wenderoth, Lind & Ponack, L.L.P.

(57) ABSTRACT

A liquid sample measurement apparatus of the present invention is provided with a timer for measuring the time from when a biosensor is attached to a liquid sample measurement device which measures the concentration of a specific component in a liquid sample that is applied to the biosensor to when the liquid sample is applied to the biosensor, and correction based on the time measured by the timer is performed to the measurement result of the concentration of the specific component in the liquid sample that is applied to the biosensor. Thereby, the measurement precision can be enhanced with utilizing the correction algorithm in which the ambient temperature and the temperature of the biosensor itself are considered.

11 Claims, 13 Drawing Sheets

Fig.4(a)

T=1.0 sec

| glucose concentration \ temperature | 15°C | 20°C | 25°C | 30°C |
|---|---|---|---|---|
| 25 mg/dl | -18% | -24% | -22% | -14% |
| 50 mg/dl | -15% | -19% | -20% | -13% |
| 100 mg/dl | -7% | -11% | -12% | -11% |
| 150 mg/dl | -6% | -8% | -10% | -7% |
| 200 mg/dl | -5% | -5% | -5% | -3% |

Fig.4(b)

T=5.0 sec

| glucose concentration \ temperature | 15°C | 20°C | 25°C | 30°C |
|---|---|---|---|---|
| 25 mg/dl | -15% | -18% | -17% | -11% |
| 50 mg/dl | -12% | -14% | -15% | -10% |
| 100 mg/dl | -5% | -8% | -9% | -8% |
| 150 mg/dl | -4% | -6% | -7% | -5% |
| 200 mg/dl | -4% | -4% | -4% | -2% |

Fig.4(c)

T=15.0 sec

| glucose concentration \ temperature | 15°C | 20°C | 25°C | 30°C |
|---|---|---|---|---|
| 25 mg/dl | -3% | -3% | -3% | -2% |
| 50 mg/dl | -2% | -2% | -2% | -2% |
| 100 mg/dl | -1% | -1% | -2% | -1% |
| 150 mg/dl | -1% | -1% | -1% | -1% |
| 200 mg/dl | -1% | -1% | -1% | 0% |

Fig.5

| glucose concentration / hematocrit value | 10 (mg/dl) | 50 (mg/dl) | 100 (mg/dl) | 200 (mg/dl) |
|---|---|---|---|---|
| Hct 70% | 2.0 | 1.7 | 1.5 | 1.0 |
| Hct 60% | 1.7 | 1.5 | 1.3 | 1.0 |
| Hct 50% | 1.5 | 1.3 | 1.0 | 1.0 |
| Hct 40% | 1.0 | 1.0 | 1.0 | 1.0 |

Fig.10(a)

T=1.0 sec

| temperature / lactic acid concentration | 15°C | 20°C | 25°C | 30°C |
|---|---|---|---|---|
| 25 mg/dl | -8.0% | -9.6% | -10.7% | -7.5% |
| 50 mg/dl | -3.5% | -4.3% | -4.7% | -3.3% |
| 75 mg/dl | -2.3% | -2.8% | -3.1% | -2.2% |
| 100 mg/dl | -0.9% | -1.1% | -1.2% | -0.8% |

Fig.10(b)

T=5.0 sec

| temperature / lactic acid concentration | 15°C | 20°C | 25°C | 30°C |
|---|---|---|---|---|
| 25 mg/dl | -4.6% | -5.5% | -6.1% | -4.3% |
| 50 mg/dl | -2.1% | -2.5% | -2.8% | -2.0% |
| 75 mg/dl | -1.1% | -1.3% | -1.5% | -1.0% |
| 100 mg/dl | -0.5% | -0.6% | -0.7% | -0.5% |

Fig.10(c)

T=15.0 sec

| temperature / lactic acid concentration | 15°C | 20°C | 25°C | 30°C |
|---|---|---|---|---|
| 25 mg/dl | -1.5% | -1.8% | -2.0% | -1.4% |
| 50 mg/dl | -0.7% | -0.8% | -0.9% | -0.6% |
| 75 mg/dl | -0.4% | -0.4% | -0.5% | -0.3% |
| 100 mg/dl | 0.0% | 0.0% | 0.0% | 0.0% |

LIQUID SAMPLE MEASUREMENT METHOD AND APPARATUS

This application is a Divisional application of Ser. No. 12/307,340, filed Jan. 2, 2009 which is the National Stage of International Application No. PCT/JP2007/063336, filed Jul. 4, 2007.

TECHNICAL FIELD

The present invention relates to liquid sample measurement method and apparatus for determining the quantity of a specific component in a liquid sample using a biosensor.

BACKGROUND ART

A biosensor is a sensor which applies a biological material to a molecule identification element by utilizing a molecule recognition ability of the biological material such as a microorganism, an enzyme, or an antibody. To be specific, the biosensor utilizes a reaction which occurs when an immobilized biological material recognizes a target specific component, consumption of oxygen by respiration of a micro-organism, an enzyme reaction, luminescence or the like. Especially, practical use of a biosensor utilizing an enzyme reaction has been progressed, and it is utilized in the medical field and the food field.

Hereinafter, an example of a biosensor measurement system utilizing an enzyme reaction will be described with reference to FIG. 13.

A biosensor measurement system 20 includes a biosensor 30 having a sample application part 30a at its front end, and a measurement unit 21 which measures the concentration of a specific component in a liquid sample that is applied to the sample application part 30a.

The measurement unit 21 includes a display part 22 which displays the measurement result, and a support part 23 in which the biosensor 30 is inserted.

The biosensor 30 is obtained by laminating a cover 31, a spacer 33, a reagent layer 35, and an insulating substrate 36 as shown in FIG. 14. The cover 31 has an vent hole 32 in its center. The spacer 33 has an approximately rectangular sample supply channel 34. The reagent layer 35 supports a reagent which enzymatically reacts with the specific component in the liquid sample. The insulating substrate 36 comprises polyethylene terephthalate or the like, and an electrode layer is formed at its surface. The electrode layer is divided by a laser or the like, thereby forming a working electrode 37, a detection electrode 38, and a counter electrode 39.

Next, a liquid sample measurement method by the biosensor measurement system 20 will be described. The description will be given of a case of measuring the glucose concentration in blood.

When the biosensor 30 is inserted in the support part 23 of the measurement unit 21, a constant voltage is applied between the working electrode 37 and the counter electrode 39.

When blood is applied to the sample application part 30a of the biosensor 30, the blood penetrates along the sample supply channel 34 by capillary phenomenon to reach the reagent layer 35, and then an enzyme reaction occurs between glucose in the blood and the reagent supported by the reagent layer 35. A change in current between the working electrode 37 and the counter electrode 39 which occurs upon the enzyme reaction is detected. Then, the glucose concentration in the blood is calculated based on the detected current change value, and the calculation result is displayed on the display part 22 of the measurement unit 21.

By the way, since the enzyme reaction has a large temperature dependence, the measurement precision is degraded due to a temperature change or the like during the measurement.

So, in order to improve the measurement precision, there has been proposed a biosensor measurement system in which a measurement apparatus is provided with a temperature correction algorithm for correcting the measurement result according to the ambient temperature during the measurement by using a temperature correction table which shows the relations between prepared glucose concentrations and temperature correction amounts (Patent Document 1).

Furthermore, as biosensor measurement systems for improving the measurement precision, there have been proposed a biosensor measurement system which measures the temperature of the biosensor itself with a thermal conductive layer provided on the insulating substrate 36 of the biosensor 30, and corrects the measurement result on the basis of the temperature of the biosensor itself (Patent Documents 2 and 3), and a biosensor measurement system having a temperature detector at the support part 23 of the measurement device 21, which measures the temperature of the biosensor 30 itself by bringing the biosensor 30 inserted in the support part 23 in contact with the temperature detector, and corrects the measurement result on the basis of the temperature of the biosensor itself (Patent Document 4).

Patent Document 1: Japanese Unexamined Patent Publication No. Hei. 8-503304
Patent Document 2: Japanese Published Patent Application No. 2001-235444
Patent Document 3: Japanese Published Patent Application No. 2003-42995
Patent Document 4: International Publication No. 2003/062812

DISCLOSURE OF THE INVENTION

Problems to be Solved by the Invention

The temperature correction algorithm installed in the conventional biosensor measurement system as disclosed in Patent Document 1 does not measure the temperature of an actual sample but measures the ambient temperature surrounding the measurement device and regards this value as the temperature of the sample. However, the biosensors which are commonly used at present are mostly handled with bare hands of users, and the heat of the finger tips of the user is conducted to the biosensor to locally change the temperature of the biosensor, and thereby the actual sample temperature might differ from the ambient temperature. Especially in self blood glucose measurement systems for diabetic patients, the user inserts the sensor into the measurement unit directly with his hand. In recent years, such self blood glucose measurement sensors have been advanced in miniaturization, and most of them are configured such that the user's hand touches the vicinity of the reagent reaction part when the user inserts the sensor into the measurement unit. If measurement is started in such state, since the surrounding ambient temperature read by a thermistor of the measurement device differs from the sample temperature, appropriate correction cannot be performed and a value that is significantly deviated from the true value is undesirably indicated. It is supposed that such problem frequently occurs especially when the analyte measurement is performed immediately after the insertion of the biosensor into the measurement device, for example, when a nurse or an operator measures the analyte of a patient or when a parent having a diabetic child helps the measurement, and it is one of major challenges to further improve the measurement precision.

On the other hand, although the biosensor measurement system proposed in Patent Document 2 or 3 can gain the temperature of the biosensor itself, since the biosensor itself must be provided with the thermistor, the biosensor becomes expensive, and therefore, it is not practical when the biosensor is disposable. Further, since such biosensor measurement system depends on temperature measurement by the thermal conductive layer, it is poor in reproducibility and requires a long measurement time.

Furthermore, since the biosensor measurement system proposed in Patent Document 4 requires the temperature detector provided in the measurement device, the cost is increased and the measurement precision might be deteriorated when the measurement time is short.

Moreover, the measurement time tends to be reduced in recent biosensor measurement systems. For example, in blood glucose measurement, measurement is completed in about five seconds after blood is applied to the sensor. Therefore, the influences of not only the surrounding ambient temperature but also the actual temperature of the reaction part on the measurement result are increased, and a biosensor measurement system of higher measurement precision is desired.

The present invention is made to solve the above-described problems and has for its object to provide a method and an apparatus for measuring a liquid sample, which can reduce measurement errors with a simple configuration while considering the influence of temperature on the measurement precision.

Measures to Solve the Problems

In order to solve the above-described problems, there is provided a liquid sample measurement method of attaching a biosensor to a measurement device and measuring the concentration of a specific component in a liquid sample that is applied to the biosensor, which method includes the steps of measuring the time from when the biosensor is attached to the measurement device to when the liquid sample is applied to the sensor; and performing correction for the measurement result of the concentration of the specific component in the liquid sample that is applied to the biosensor, on the basis of the measured time.

According to the present invention, there is provided a liquid sample measurement method of attaching a biosensor to a measurement device and measuring the concentrations of plural specific components in a liquid sample that is applied to the biosensor, which method includes the steps of measuring the time from when the biosensor is attached to the measurement device to when the liquid sample is applied to the sensor; and performing corrections for the respective measurement results of the concentrations of the plural specific components in the liquid sample that is applied to the biosensor, on the basis of the measured time.

According to the present invention, there is provided a liquid sample measurement method of attaching plural biosensors of different types to a measurement device and measuring the concentrations of specific components in liquid samples that are applied to the respective biosensors, which method includes the steps of measuring the time from when each of the biosensors is attached to the measurement device to when the liquid sample is applied to the sensor; and performing correction for the measurement result of the concentration of the specific component in the liquid sample that is applied to the biosensor, on the basis of the measured time and the type of the biosensor.

According to the present invention, in the liquid sample measurement method described above, the amount of correction for the measurement result of the concentration of the specific component in the liquid sample that is applied to the biosensor is varied according to the measured time from when the biosensor is attached to the measurement device to when the liquid sample is applied to the sensor.

According to the present invention, in the liquid sample measurement method described above, the amount of correction is reduced when the measured time from when the biosensor is attached to the measurement device to when the liquid sample is applied to the sensor is long.

According to the present invention, in the liquid sample measurement method described above, whether correction should be performed or not for the measurement result of the concentration of the specific component in the liquid sample that is applied to the biosensor is judged according to the measured time from when the biosensor is attached to the measurement device to when the liquid sample is applied to the sensor.

According to the present invention, in the liquid sample measurement method described above, the correction is performed when the measured time from when the biosensor is attached to the measurement device to when the liquid sample is applied to the sensor is within a specific time period.

According to the present invention, in the liquid sample measurement method described above, the amount of correction for the measurement result is determined according to the measurement result of the concentration of the specific component in the liquid sample that is applied to the biosensor.

According to the present invention, in the liquid sample measurement method described above, the amount of correction for the measurement result of the concentration of the specific component in the liquid sample that is applied to the biosensor is determined according to the ambient temperature at the measurement.

According to the present invention, in the liquid sample measurement method described above, the amount of correction for the measurement result of the concentration of the specific component in the liquid sample that is applied to the biosensor is determined according to a second specific component which exists in the liquid sample and is other than said specific component.

According to the present invention, in the liquid sample measurement method described above, the liquid sample is blood, and the amount of correction is determined according to the hematocrit value of the blood.

According to the present invention, there is provided a liquid sample measurement method of attaching a biosensor to a measurement device and measuring the concentration of a specific component of a liquid sample that is applied to the sensor, which method includes the steps of measuring the time from when the biosensor is attached to the measurement device to when the liquid sample is applied to the sensor, and the ambient temperature at the measurement; correcting the measured ambient temperature on the basis of the measured time from when the biosensor is attached to the measurement device to when the liquid sample is applied to the sensor; and correcting the measurement result of the concentration of the specific component in the liquid sample that is applied to the biosensor, on the basis of the corrected ambient temperature.

According to the present invention, in the liquid sample measurement method described above, the amount of correction for the measurement result is determined according to the kind of the liquid sample that is applied to the biosensor.

According to the present invention, there is provided a liquid sample measurement apparatus having a biosensor attached thereto, which measures the concentration of a specific component in a liquid sample that is applied to the biosensor, including: a time measurement means for measuring the time from when the biosensor is attached to when the liquid sample is applied to the sensor; and a measurement result correction means for correcting the measurement result of the concentration of the specific component in the liquid sample that is applied to the biosensor, on the basis of the time measured by the time measurement means.

According to the present invention, in the liquid sample measurement apparatus described above, the measurement result correction means changes the amount of correction for the measurement result of the concentration of the specific component in the liquid sample that is applied to the biosensor, according to the time measured by the time measurement means.

According to the present invention, in the liquid sample measurement apparatus described above, the measurement result correction means reduces the amount of correction when the time measured by the time measurement means is long.

According to the present invention, in the liquid sample measurement apparatus described above, the measurement result correction means judges whether correction should be performed or not for the measurement result of the concentration of the specific component in the liquid sample that is applied to the biosensor, according to the time measured by the time measurement means.

According to the present invention, in the liquid sample measurement apparatus described above, the measurement result correction means performs said correction when the time measured by the time measurement means is within a specific time.

According to the present invention, in the liquid sample measurement apparatus described above, the measurement result correction means determines the amount of correction for the measurement result according to the measurement result of the concentration of the specific component in the liquid sample that is applied to the biosensor.

According to the present invention, the liquid sample measurement apparatus described above further includes a temperature measurement part for measuring the ambient temperature at the measurement, and the measurement result correction means determines the amount of correction for the measurement result of the concentration of the specific component in the liquid sample that is applied to the biosensor, according to the ambient temperature measured by the temperature measurement part.

According to the present invention, in the liquid sample measurement apparatus described above, the measurement result correction means determines the amount of correction for the measurement result of the concentration of the specific component in the liquid sample that is applied to the biosensor, according to a second specific component which exists in the liquid sample and is other than said specific component.

According to the present invention, in the liquid sample measurement apparatus described above, the liquid sample is blood, and the second specific component is the hematocrit value of the blood.

According to the present invention, in the liquid sample measurement apparatus described above, the measurement result correction means determines the amount of correction for the measurement result according to the type of the liquid sample that is applied to the biosensor.

According to the present invention, there is provided a liquid sample measurement apparatus having a biosensor attached thereto, which measures the concentration of a specific component in a liquid sample that is applied to the biosensor, including: a time measurement means for measuring the time from when the biosensor is attached to when the liquid sample is applied to the sensor; a temperature sensor for measuring the ambient temperature at measurement; a temperature correction means for correcting the ambient temperature measured by the temperature sensor, on the basis of the time measured by the time measurement means; and a measurement result correction means for performing correction for the measurement result of the concentration of the specific component in the liquid sample that is applied to the biosensor, on the basis of the corrected ambient temperature.

Effects of the Invention

According to the present invention, in a liquid sample measurement method of attaching a biosensor to a measurement device and measuring the concentration of a specific component in a liquid sample that is applied to the sensor, the time from when the biosensor is attached to the measurement device to when the liquid sample is applied to the sensor is measured, and the measurement result of the concentration of the specific component in the liquid sample that is applied to the biosensor is corrected based on the measured time. Therefore, when measuring the concentration of the specific component in the liquid sample, the ambient temperature and the temperature of the sensor itself are prevented from adversely affecting the measurement result, thereby obtaining a highly-precise measurement result when the measurement time is short.

Further, according to the present invention, in a liquid sample measurement method of attaching a biosensor to a measurement device and measuring the concentrations of plural specific components in a liquid sample that is applied to the biosensor, the time from when the biosensor is attached to the measurement device to when the liquid sample is applied to the sensor is measured, and the measurement results of the concentrations of the plural specific components in the liquid sample that is applied to the biosensor are respectively corrected based on the measured time. Therefore, when measuring the concentration of the specific component in the liquid sample, the ambient temperature and the temperature of the sensor itself are prevented from adversely affecting the measurement result, thereby obtaining a highly-precise measurement result when the measurement time is short.

Further, according to the present invention, in a liquid sample measurement method of attaching plural biosensors of different types to a measurement device and measuring the concentrations of specific components in liquid samples that are applied to the respective biosensors, the time from when each of the biosensors is attached to the measurement device to when the liquid sample is applied to the sensor is measured, and the measurement result of the concentration of the specific component in the liquid sample that is applied to the biosensor is corrected based on the measured time and the type of the biosensor. Therefore, when measuring the concentration of the specific component in the liquid sample, the ambient temperature and the temperature of the sensor itself are prevented from adversely affecting the measurement result, thereby obtaining a highly-precise measurement result when the measurement time is short.

Further, according to the present invention, in a liquid sample measurement method of attaching a biosensor to a measurement device and measuring the concentration of a specific component of a liquid sample that is applied to the sensor, the time from when the biosensor is attached to the measurement device to when the liquid sample is applied to the sensor and the ambient temperature at the measurement are measured, the measured ambient temperature is corrected based on the measured time from when the biosensor is attached to the measurement device to when the liquid sample is applied to the sensor, and the measurement result of the concentration of the specific component in the liquid sample that is applied to the biosensor is corrected based on the corrected ambient temperature. Therefore, when measuring the concentration of the specific component in the liquid sample, the ambient temperature and the temperature of the sensor itself are prevented from adversely affecting the measurement result, thereby obtaining a highly-precise measurement result when the measurement time is short.

Further, according to the present invention, a liquid sample measurement apparatus having a biosensor attached thereto, which measures the concentration of a specific component in a liquid sample that is applied to the biosensor, includes a time measurement means for measuring the time from when the biosensor is attached to when the liquid sample is applied to the sensor, and a measurement result correction means for correcting the measurement result of the concentration of the specific component in the liquid sample that is applied to the biosensor, on the basis of the time measured by the time measurement means. Therefore, when measuring the concentration of the specific component in the liquid sample, the ambient temperature and the temperature of the sensor itself are prevented from adversely affecting the measurement result, thereby realizing an apparatus which can improve the measurement precision even when the measurement time is short.

Further, according to the present invention, a liquid sample measurement apparatus having a biosensor attached thereto, which measures the concentration of a specific component in a liquid sample that is applied to the biosensor, includes a time measurement means for measuring the time from when the biosensor is attached to when the liquid sample is applied to the sensor, a temperature sensor for measuring the ambient temperature at measurement, a temperature correction means for correcting the ambient temperature measured by the temperature sensor, on the basis of the time measured by the time measurement means, and a measurement result correction means for performing correction for the measurement result of the concentration of the specific component in the liquid sample that is applied to the biosensor, on the basis of the corrected ambient temperature. Therefore, when measuring the concentration of the specific component in the liquid sample, the ambient temperature and the temperature of the sensor itself are prevented from adversely affecting the measurement result, thereby realizing an apparatus which can improve the measurement precision even when the measurement time is short.

BRIEF DESCRIPTION OF THE DRAWINGS

FIG. 4 is a diagram illustrating examples of correction tables which are used when performing correction to the measurement result of concentration of a specific component in an analyte that is applied to the biosensor in the biosensor measurement system of the first embodiment.

FIG. 5 is a diagram illustrating an example of a correction table which is used when performing correction to the measurement result of concentration of a specific component in blood as an analyte that is applied to the biosensor in the biosensor measurement system of the first embodiment.

FIG. 10 is a diagram illustrating examples of correction tables to be used when correcting the measurement result of lactic acid concentration in an analyte that is applied to the biosensor in the biosensor measurement system of the third embodiment.

DESCRIPTION OF REFERENCE NUMERALS

Figure 1:
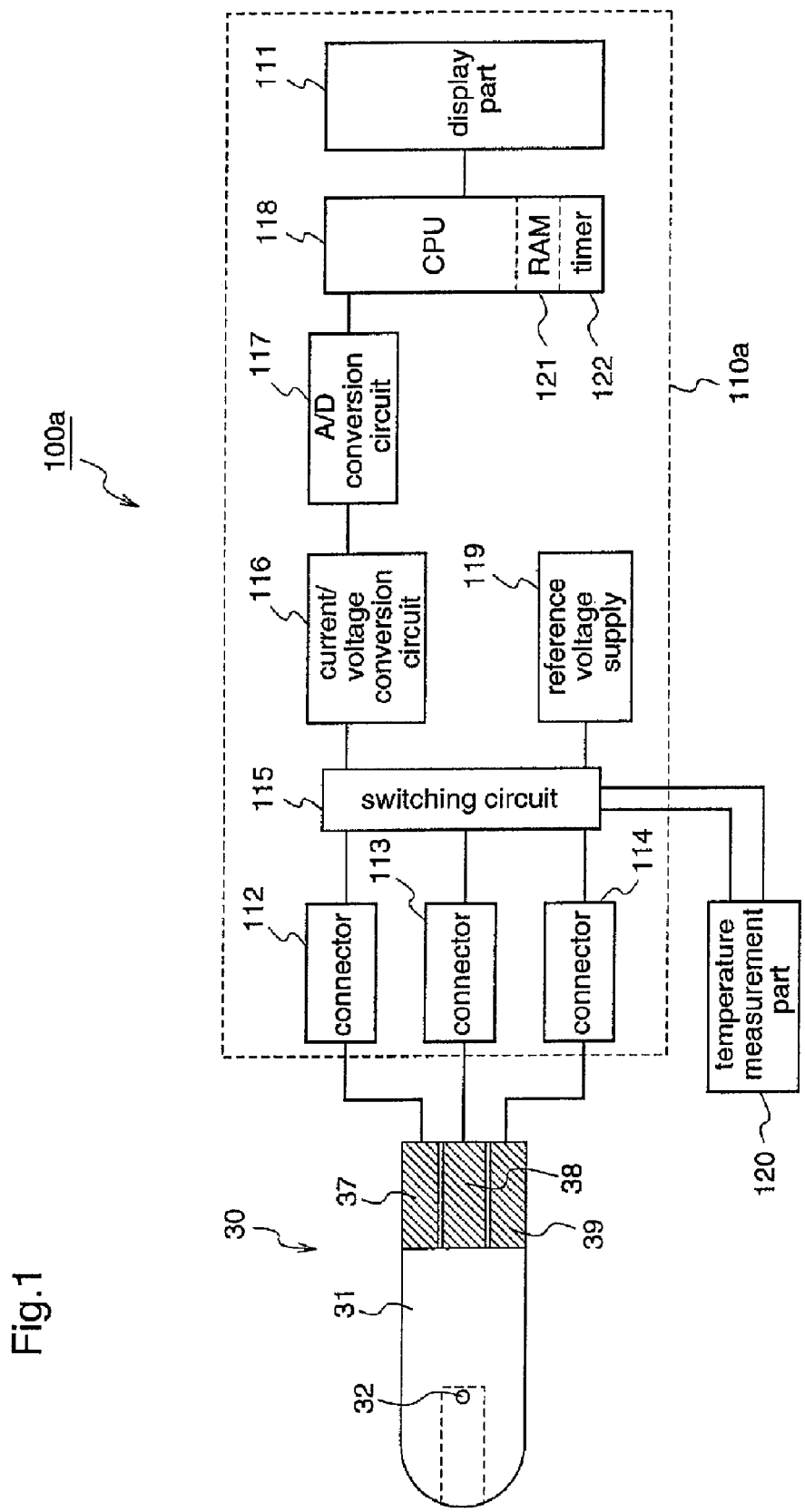
FIG. 1 is a diagram illustrating an example of configuration of a biosensor measurement system according to a first embodiment of the present invention.
Figure 2:
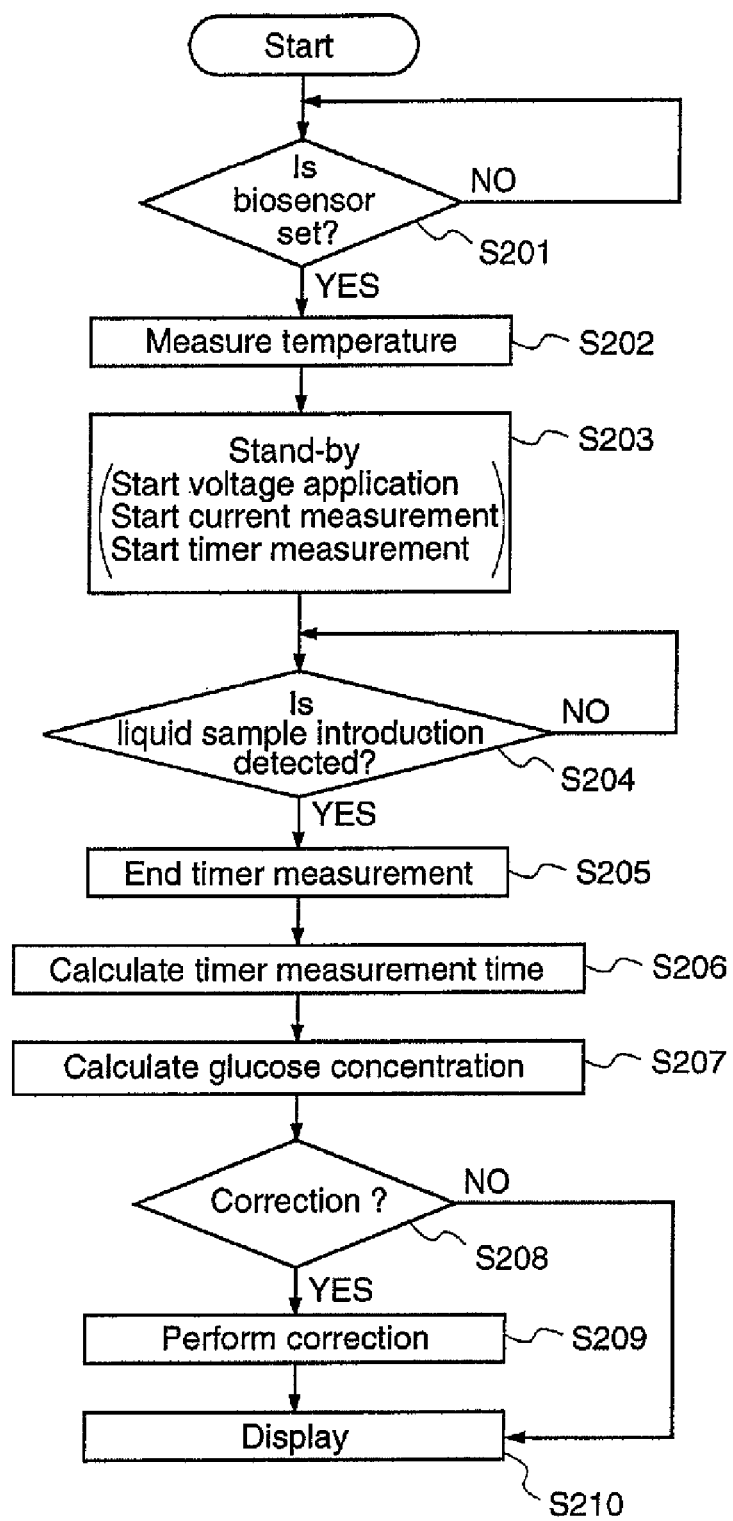
FIG. 2 is a diagram illustrating a liquid sample measurement method by the biosensor measurement system of the first embodiment.

20 . . . biosensor measurement system
21 . . . measurement device
22 . . . display part
23 . . . support part
30 . . . biosensor
30$a$ . . . sample application part
31 . . . cover
32 . . . vent hole
33 . . . spacer
34 . . . sample supply channel
35 . . . reagent layer
36 . . . insulating substrate
37 . . . working electrode
38 . . . detection electrode
39 . . . counter electrode
100$a$,100$b$ . . . biosensor measurement system
110$a$,110$b$ . . . measurement device
112,113,114,123,124,125,126,127 . . . connector 115 . . . switching circuit
116 . . . current/voltage conversion circuit
117 . . . A/D conversion circuit
118 . . . CPU
119 . . . reference voltage supply
120 . . . thermistor
121 . . . RAM
122 . . . timer
700 . . . biosensor
700a . . . sample application part
701 . . . cover
702 . . . vent hole
703 . . . spacer
704 . . . sample supply channel
705 . . . reagent layer for lactic acid measurement
706 . . . reagent layer for glucose measurement
707 . . . working electrode for lactic acid measurement
708 . . . working electrode for glucose measurement
709 . . . detection electrode
710 . . . counter electrode for glucose measurement
711 . . . counter electrode for lactic acid measurement
712 . . . insulating substrate

BEST MODE TO CARRY OUT THE INVENTION

Hereinafter, preferred embodiments of the present invention will be described with reference to the drawings.

Embodiment 1

Hereinafter, a biosensor measurement system according to a first embodiment of the present invention will be described. In this embodiment, blood is used as an analyte.

FIG. 1 is a diagram illustrating the configuration of the biosensor measurement system of the first embodiment.

Figure 13:
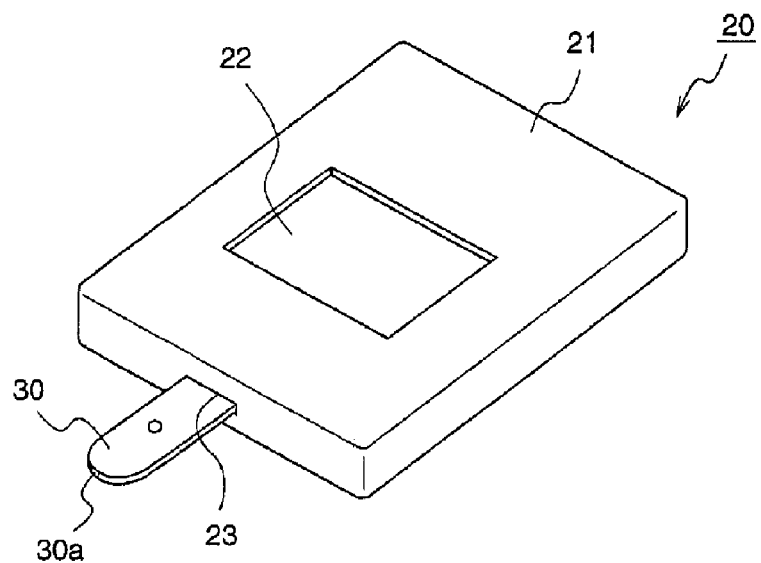
FIG. 13 is a diagram illustrating an example of the conventional biosensor measurement system.

The biosensor measurement system 100a of the first embodiment is provided with a biosensor 30 and a measurement device 110a. The exterior appearance of the biosensor measurement system 100a is identical to the conventional one shown in FIG. 13, and the measurement device 110a is provided with a display part for displaying the measurement result, and a support part in which the biosensor is inserted.

Figure 14:
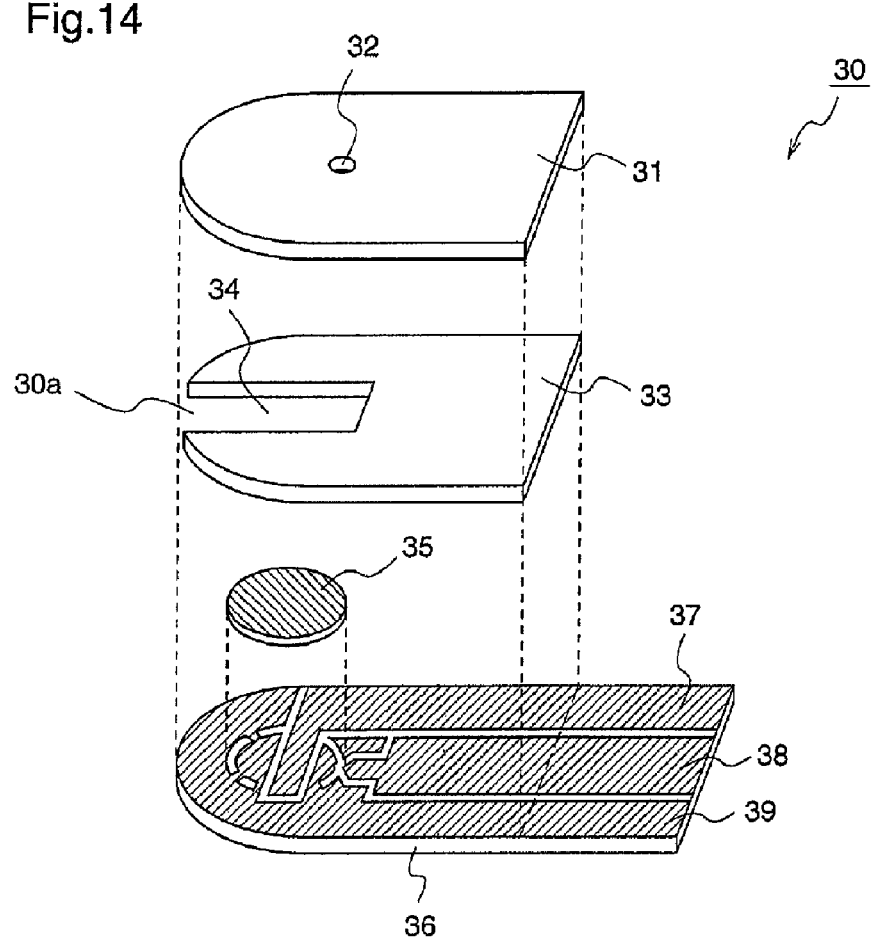
FIG. 14 is an exploded perspective view illustrating an example of configuration of a biosensor.

As shown in FIG. 14, the biosensor 30 is obtained by laminating a cover 31, a spacer 33, a reagent layer 35, and an insulating substrate 36. The cover 31 has an vent hole 32 in its center. The spacer 33 has an approximately rectangle-shaped sample supply channel 34. The reagent layer 35 supports a reagent which enzymatically reacts with a specific component in a liquid sample. The insulating substrate 36 comprises polyethylene terephthalate or the like, and an electrode layer is formed at its surface. The electrode layer is divided to a working electrode 37, a detection electrode 38, and a counter electrode 39 by a laser or the like.

The measurement device 110a is provided with a display part 111, connectors 112, 113, and 114, a switching circuit 115, a current/voltage conversion circuit 116, an A/D conversion circuit 117, a CPU 118, a reference voltage supply 119, a temperature sensor 120, a RAM 121, and a time measurement means (timer) 122.

The connectors 112, 113, and 114 contact the working electrode 37, the detection electrode 38, and the counter electrode 39 of the biosensor 30, respectively. The switching circuit 115 switches the connections between the connectors 112 to 114 and the reference voltage supply 119 and the connections between the connectors 112 to 114 and the current/voltage conversion circuit 116. The current/voltage conversion circuit 116 converts a current that flows between the working electrode 37 and the other electrodes 38 and 39 into a voltage. The A/D conversion circuit 117 converts an output value from the current/voltage conversion circuit 116 into a pulse. The CPU 118 calculates the concentration of the specific component in the liquid sample on the basis of the pulse from the A/D conversion circuit 117. The reference voltage supply 119 applies a voltage to the connectors 112 to 114. The temperature sensor 120 measures the temperature of the measurement environment. The timer 122 measures the time required from when the biosensor 30 is inserted in the support part of the measurement device 110a to when the liquid sample is applied to the sensor 30. The RAM 121 stores a temperature correction table (not shown) for determining the amount of correction for the measurement result of the concentration of the specific component in the liquid sample applied to the biosensor 30 on the basis of the ambient temperature, and a correction table (refer to FIGS. 3 and 4) for determining the amount of correction for the measurement result of the concentration of the specific component in the liquid sample applied to the biosensor 30 on the basis of the time from when the biosensor 30 is set in the measurement device 110a to when introduction of the analyte is detected. A ROM may be used to store the correction tables.

Hereinafter, the features of the biosensor measurement system 100a of the first embodiment will be described in comparison with the conventional one.

Although the conventional biosensor measurement system 20 previously stores the temperature correction table showing the correction amounts based on the glucose concentration and the ambient temperature into the measurement device 21 to perform temperature correction using the temperature correction table for the measurement result of the glucose concentration in the blood that is applied to the biosensor 30, the following drawbacks have occurred according to the time up to the start of measurement.

Figure 3A:
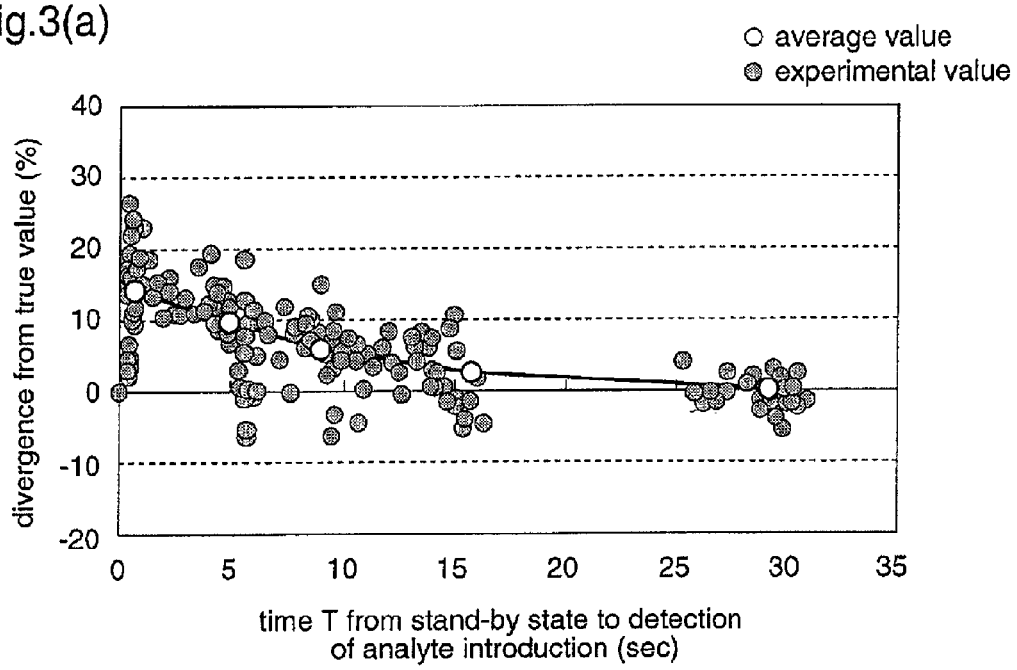
FIG. 3($a$) is a graph illustrating sensor response values obtained when using the conventional biosensor measurement system, and FIG. 3($b$) is a graph illustrating sensor response values obtained when using the biosensor measurement system of the first embodiment.

FIG. 3(a) shows the measurement result obtained by the conventional biosensor measurement system 20. The abscissa shows the time T(sec) from when the biosensor 30 is inserted in the measurement device 21 to when blood is applied to the sensor 30, and the ordinate shows the degree of divergence (%) from the true value. The measurement was performed at an ambient temperature of 25° C., using an analyte which was prepared at a glucose concentration of 100 mg/dl (hematocrit value of 40%). At this time, the biosensor 30 was inserted in the measurement device 21 by six donors having different fingertip temperatures, and the time T until the analyte was applied to the sensor 30 after insertion of the sensor 30 was measured within a range from 0.01 to 30 sec.

As can be seen from FIG. 3(a), the degree of divergence from the true value is larger as the time T is shorter. That is, it is considered that the fingertip heat influences on the measurement result.

On the other hand, the biosensor measurement system 100a of this first embodiment performs correction for the measurement result (this measurement result is a value obtained after temperature correction) of the glucose concentration in the blood that is applied to the biosensor 30 on the basis of the time T from when the biosensor 30 is inserted in the measurement device 110a to when the blood is applied to the sensor 30.

The amount of correction for the measurement result of the glucose concentration in the blood is determined based on the degree of divergence from the true value. For example, when time T is 1.0 sec, since the degree of divergence from the true value is +14% as shown in FIG. 3(a), the correction amount in the case where the temperature is 25° C., and the glucose concentration is 100 mg/dl is determined at −12%, and correction is performed for the measurement result of the glucose concentration in the blood that is applied to the biosensor 30. Likewise, correction is performed for the measurement result with the correction amount being set at −9% when the time T is 5.0 sec and with the correction amount being set at −2% when the time T is 15.0 sec.

Figure 3B:
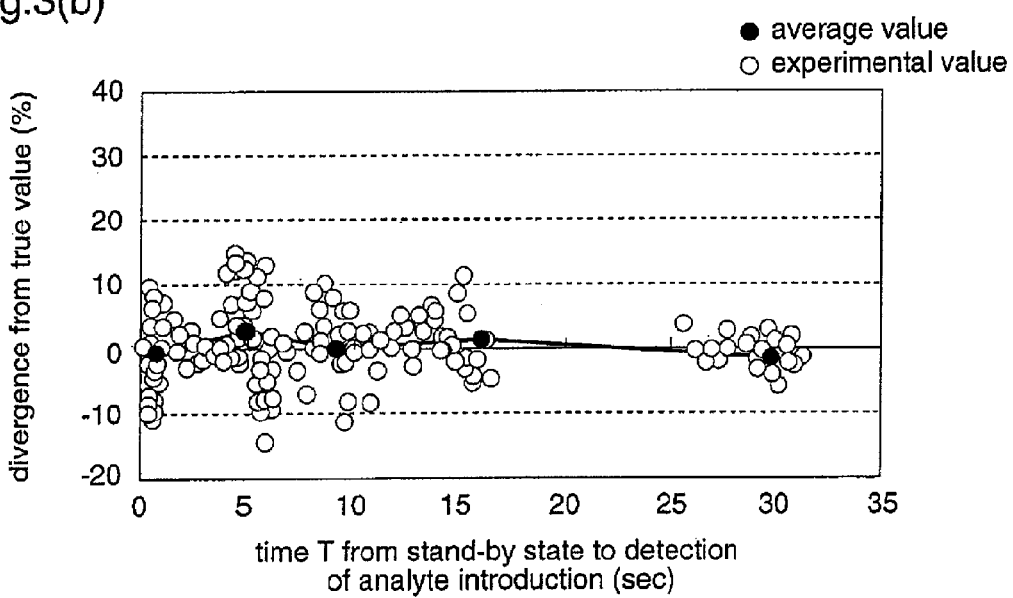

Since the measurement result of the glucose concentration in the blood that is applied to the biosensor 30 is thus corrected based on the time T, the degree of divergence from the true value can be minimized even when the time T is within 20 sec as shown in FIG. 3(b), thereby improving the measurement precision.

Further, in the biosensor measurement system 100a of this first embodiment, not only the time T but also the glucose concentration and the ambient temperature are added as correction parameters as shown in FIG. 4 in order to dramatically improve the measurement precision. This is because the influence of the fingertip heat on the measurement result differs depending on the glucose concentration and the ambient temperature.

FIG. 4(a) is a correction table showing the correction amounts (%) when the time T is 1.0 sec, FIG. 4(b) is a correction table showing the correction amounts (%) when the time T is 5.0 sec, and FIG. 4(c) is a correction table showing the correction amounts (%) when the time T is 15.0 sec. The ordinate shows the glucose concentration and the abscissa shows the temperature. The numerical values on the tables shown in FIG. 4 are merely examples, and the correction amounts are not restricted thereto. Further, the number of tables is also not restricted to those shown in FIG. 4, and the measurement precision can be more improved as the number of tables becomes larger.

Next, the method of calculating the correction amounts using the correction tables shown in FIG. 4 will be described.

For example, when the ambient temperature is 25° C., the final response value is 100 mg/dl, and the time T is 1.0 sec, it is found from FIG. 4(a) that the correction amount is −12%. Further, it is found from FIG. 4(b) that the correction amount is −9% when the time T is 5.0 sec, and it is found from FIG. 4(c) that the correction amount is −2% when the time T is 15.0 sec.

Furthermore, when the time T is 3.0 sec, the correction amount at T=3.0 sec is calculated as −10.5% by linearly regressing the correction amount (−12%) at T=1.0 sec and the correction amount (−9%) at T=5.0 sec.

Further, when the liquid sample is blood, the influence of the fingertip heat varies depending on the hematocrit value in the blood. So, a correction table in which the hematocrit value is newly added as a correction parameter as shown in FIG. 5 is combined with the correction tables shown in FIG. 4 to be used for the correction, thereby improving the measurement precision. FIG. 5 shows a correction table for determining the correction rate from the relation between the hematocrit value and the glucose concentration. The numerical values on the table shown in FIG. 5 are merely examples, and the correction amounts are not restricted thereto. Further, the glucose concentrations and the hematocrit values are also not restricted to those shown in FIG. 5.

While in this first embodiment the hematocrit value is used as the second specific component when measuring the glucose concentration, oxidizable substances such as ascorbic acid, uric acid, acetaminophen and the like may be used as the second specific component, and moreover, other predispositions that cause changes in the influence of the fingertip heat may be used as the second specific component.

Next, the liquid sample measurement method by the biosensor measurement system 100a of this first embodiment will be described.

When the biosensor 30 is set in the support part of the measurement device 110a, it is judged by a switch in the support part whether the biosensor 30 is inserted or not. When it is detected that the biosensor 30 is inserted, the power supply of the measurement device 110a is automatically turned on (step S201). Then, the ambient temperature is measured by the temperature sensor 120 (step S202), and the measurement device 110a goes into the analyte introduction stand-by state (step S203). The analyte introduction stand-by state is the state after starting voltage application from the reference voltage supply 119 to the connectors 112 to 114, starting current measurement by the current/voltage conversion circuit 116, and starting measurement of time from when the biosensor 30 is inserted to when the analyte is applied to the sensor 30.

While in this first embodiment the power supply of the measurement device 110a is automatically turned on by the insertion of the biosensor 30, also when the power supply of the measurement device 110a is manually turned on, it is similarly judged whether the biosensor 30 is inserted or not and the measurement device 110a goes into the analyte introduction stand-by state. Then, measurement of time from when the biosensor 30 is inserted to when the analyte is applied to the sensor 30 is started by the timer 122, thereby obtaining the same effect.

When blood as the analyte is applied to the biosensor 30, the current/voltage conversion circuit 116 reads a change in the current value to detect that the analyte is introduced (applied) to the sensor 30 (step S204). The count by the timer 122 is completed upon the detection of the analyte introduction (step S205), and the time T from when the biosensor 30 is inserted in the measurement device 110a to when the analyte introduction is detected is calculated (step S206).

Then, the glucose concentration in the blood that is applied to the biosensor 30 is calculated (step S207). At this time, the correction amount is obtained from the temperature correction table stored in the RAM 121 on the basis of the ambient temperature measured in step S202, and correction is performed for the measurement result of the glucose concentration in the blood that is applied to the biosensor 30.

Thereafter, it is judged based on the time T calculated in step S206 as to whether the glucose concentration value calculated in step S207 should be corrected or not (step S208).

As for this judgment, it has previously been set to perform correction when the respective parameters are within the ranges described below.

The time T is set so as to perform correction when it is within a range from 0.01 to 60 sec. Preferably, correction should be performed when the time T is within a range from 0.01 to 30 sec, and more preferably, from 0.01 to 20 sec. The read interval of the time T is set to every 1 sec. Preferably, it is set to every 0.1 sec, and more preferably, every 0.01 sec.

The glucose concentration is set so as to perform correction when it is within a range from 10 to 800 mg/dl. Preferably, correction should be performed when it is within a range from 10 to 400 mg/dl, and more preferably, from 10 to 250 mg/dl.

The ambient temperature is set so as to perform correction when it is within a range from 5 to 45° C. Preferably, correction should be performed when it is within a range from 10 to 40° C., and more preferably, from 15 to 35° C.

When the analyte is blood, it is set to perform correction when the hematocrit value is within a range from 0 to 70%. Preferably, correction should be performed when the hematocrit value is within a range from 15 to 70%, and more preferably, from 30 to 70%. Calculation of the hematocrit value is preferably executed before the calculation of the glucose concentration (step S207), and more preferably, the glucose concentration should be corrected based on the calculated hematocrit value. Further, the hematocrit value is not necessarily measured in the biosensor. For example, the hematocrit value may be previously calculated by a large-size measurement apparatus and inputted to the measurement device.

When it is judged in step S208 that correction should be performed, the amount of correction for the measurement result of the glucose concentration in the blood that is applied to the biosensor 30 is obtained from the correction table shown in FIG. 4, and the measurement result is corrected (step S209). The corrected value is displayed on the display part of the measurement device 110a as the concentration of glucose included in the blood as the analyte (step S210). If it is judged from the time T that the reliability of the measurement result is low, an error display may be performed without displaying the measurement result, or it may be displayed that the reliability of the measurement result is low.

On the other hand, when it is judged in step S208 that correction is not necessary, the operation goes to step S210 and the value calculated in step S207 is displayed as it is. In this first embodiment, it is judged that correction is not necessary when the time T exceeds 20 sec.

By performing the aforementioned operation, more reliably correction can be carried out.

As described above, in the liquid sample measurement method and apparatus of this first embodiment, the time T from when the biosensor 30 is inserted in the measurement device 110a to when blood is applied to the sensor 30 is measured, and the measurement result of the glucose concentration in the blood applied to the biosensor 30 is corrected based on the measurement time T. Therefore, adverse effect of fingertip heat on the measurement result is avoided, and a highly-precise measurement result can be obtained even when the measurement time is short. Further, a highly-precise measurement apparatus can be realized at low cost without newly providing a temperature sensor for measuring the temperature of the biosensor 30 itself.

Further, in this first embodiment, it is possible to dramatically improve the measurement precision by adopting not only the measured time T but also the glucose concentration, the hematocrit value, the ambient temperature and the like as the correction parameters for determining the amount of correction for the measurement result of the glucose concentration in blood that is applied to the biosensor 30.

Embodiment 2

Hereinafter, a biosensor measurement system according to a second embodiment of the present invention will be described.

The biosensor measurement system of this second embodiment is configured so as to correct the ambient temperature on the basis of the time T from when the biosensor is inserted in the measurement device to when the analyte is applied to the sensor, and perform correction for the measurement result of the concentration of the specific component in the analyte that is applied to the biosensor on the basis of the corrected ambient temperature.

The configuration of the biosensor measurement system of this second embodiment is identical to that of the first embodiment shown in FIG. 1.

Figure 6:
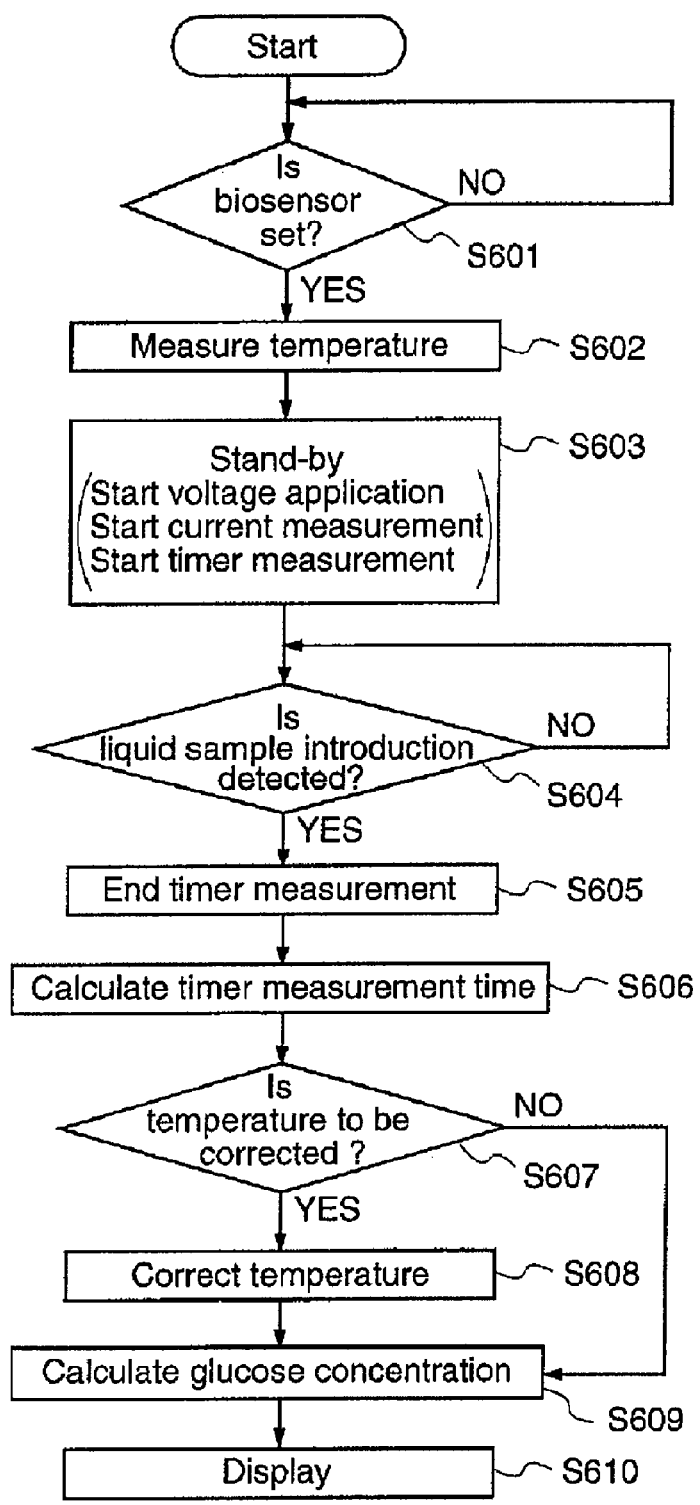
FIG. 6 is a diagram illustrating a liquid sample measurement method by a biosensor measurement system according to a second embodiment of the present invention.

Hereinafter, the liquid sample measurement method by the biosensor measurement system of the second embodiment will be described with reference to FIG. 6.

When the biosensor 30 is set in the support part of the measurement device 110a, it is judged whether the biosensor 30 is inserted or not by the switch in the support part. When it is detected that the biosensor 30 is inserted, the power supply of the measurement device 110a is automatically turned on (step S601). Then, the ambient temperature is measured by the temperature sensor 120 (step S602), and the measurement device 110a goes into the analyte introduction stand-by state (step S603). The analyte introduction stand-by state is the state after starting voltage application from the reference voltage supply 119 to the connectors 112 to 114, starting current measurement by the current/voltage conversion circuit 116, and starting measurement of time from when the biosensor 30 is inserted to when the analyte is applied to the sensor 30 using the timer 122.

When the blood as the analyte is applied to the biosensor 30, the current/voltage conversion circuit 116 reads a change in the current value to detect that the analyte is introduced (applied) to the sensor 30 (step S604). The count by the timer 122 is completed upon detecting the analyte introduction (step S605), and the time T from when the biosensor 30 is inserted in the measurement device 110a (the analyte introduction stand-by state) to when the analyte introduction is detected is calculated (step S606).

Then, whether correction should be performed or not for the temperature measured in step S602 is judged based on the time T calculated in step S606 (step S607). When it is judged in step S607 that correction should be performed, the operation goes to step S608, wherein the temperature measured in step S602 is corrected and the corrected temperature is regarded as the ambient temperature, followed by step S609. On the other hand, when it is judged in step S607 that correction is not necessary, the temperature measured in step S602 is regarded as the ambient temperature, and the operation goes to step S609.

For example, the judgement in step S607 is set such that correction should be performed when the time T is within a range from 0.01 to 60 sec. Preferably, correction should be performed when the time T is within a range from 0.01 to 30 sec, and more preferably, from 0.01 to 20 sec. The read interval of the time T is set to every 1 sec. Preferably, it is set to every 0.1 sec, and more preferably, every 0.01 sec.

For example, in the case where the measurement is performed at the ambient temperature of 25° C., the amount of correction for the measured temperature is +4° C. to correct the ambient temperature to 29° C. when time T=1.0 (sec), the amount of correction for the measured temperature is +3° C. to correct the ambient temperature to 28° C. when time T=5.0 (sec), and the amount of correction for the measured temperature is +1° C. to correct the ambient temperature to 26° C. when time T=15.0 (sec). On the other hand, since the influence of the fingertip heat on the measurement result is extremely small when time T=20.0 (sec), it is judged that correction is not necessary, and the temperature measured in step S602 is adopted as the ambient temperature.

Then, the glucose concentration in the blood that is applied to the biosensor 30 is calculated (step S609). At this time, the correction amount is obtained from the temperature correction table stored in the RAM 121 on the basis of the temperature corrected in step S608 when it is judged in step S607 that correction should be performed, or on the basis of the temperature measured in step S602 when it is judged in step S607 that correction is not necessary, and correction is performed to the measurement result of the glucose concentration in the blood that is applied to the biosensor 30.

The glucose concentration calculated in step S609 is displayed on the display part of the measurement device 110a as the concentration of glucose included in the blood as the analyte (step S610).

As described above, in the liquid sample measurement method and apparatus of this second embodiment, the ambient temperature is measured in addition to measuring the time T from when the biosensor 30 is inserted in the measurement device 110a to when blood is applied to the sensor 30, and this ambient temperature is corrected based on the time T, and then the measurement result of the glucose concentration in the blood that is applied to the biosensor 30 is corrected on the basis of the corrected ambient temperature. Therefore, adverse effect of the fingertip heat on the measurement result is avoided as in the first embodiment, and thereby a highly-precise measurement result can be obtained even when the measurement time is short. Further, a highly-precise measurement device can be realized at low cost without newly providing a temperature sensor for measuring the temperature of the biosensor 30 itself.

While in the first and second embodiments the biosensor 30 is an electrode type sensor, it may be an optical sensor.

While in the first and second embodiments blood glucose is adopted as the measurement target substance, the measurement target substance is not restricted thereto, and a biological sample such as cholesterol, triglyceride, lactic acid, uric acid, bilirubin, or alcohol, an ambient sample, or a food sample may be adopted with the same effects as described above.

Embodiment 3

Hereinafter, a biosensor measurement system according to a third embodiment of the present invention will be described.

In this third embodiment, blood is used as an analyte, and the concentrations of glucose and lactic acid as specific components in blood are simultaneously measured in a single sensor.

In the biosensor measurement system of this third embodiment, the measurement results of the concentrations of the specific components in the analyte that is applied to the biosensor are subjected to corrections most suitable for the respective specific components on the basis of the time T from when the biosensor is inserted in the measurement device to when the analyte is applied to the sensor.

Figure 7:
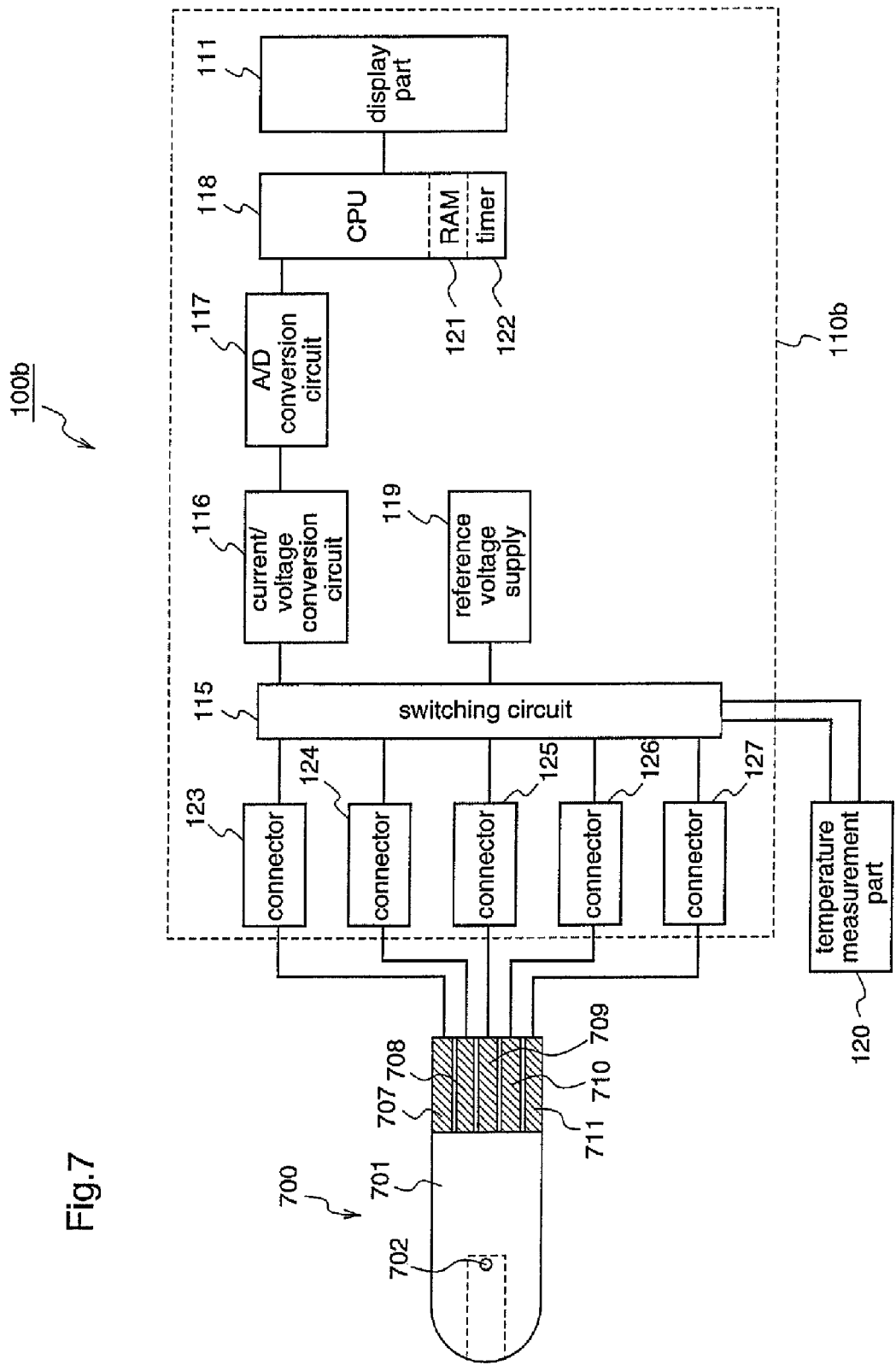
FIG. 7 is a diagram illustrating an example of configuration of a biosensor measurement system according to a third embodiment of the present invention.

FIG. 7 is a diagram illustrating the configuration of the biosensor measurement system of the third embodiment. In FIG. 7, the same constituents as those shown in FIG. 1 are given the same reference numerals.

The biosensor measurement system 100b of this third embodiment is provided with a biosensor 700 and a measurement device 110b. The exterior appearance of the biosensor measurement system 100b is identical to the conventional one shown in FIG. 13, and the measurement device 110b is provided with a display part for displaying the measurement result, and a support part in which the biosensor is inserted.

The measurement device 110b is provided with a display part 111, connectors 123, 124, 125, 126, and 127, a switching circuit 115, a current/voltage conversion circuit 116, an A/D conversion circuit 117, a CPU 118, a reference voltage supply 119, a temperature sensor 120, a RAM 121, and a timer 122.

The connectors 123, 124, 125, 126, and 127 contact a working electrode 707 for measuring lactic acid, a working electrode 708 for measuring glucose, a detection electrode 709, a counter electrode 710 for measuring glucose, and a counter electrode 711 for measuring lactic acid, respectively.

Figure 8:
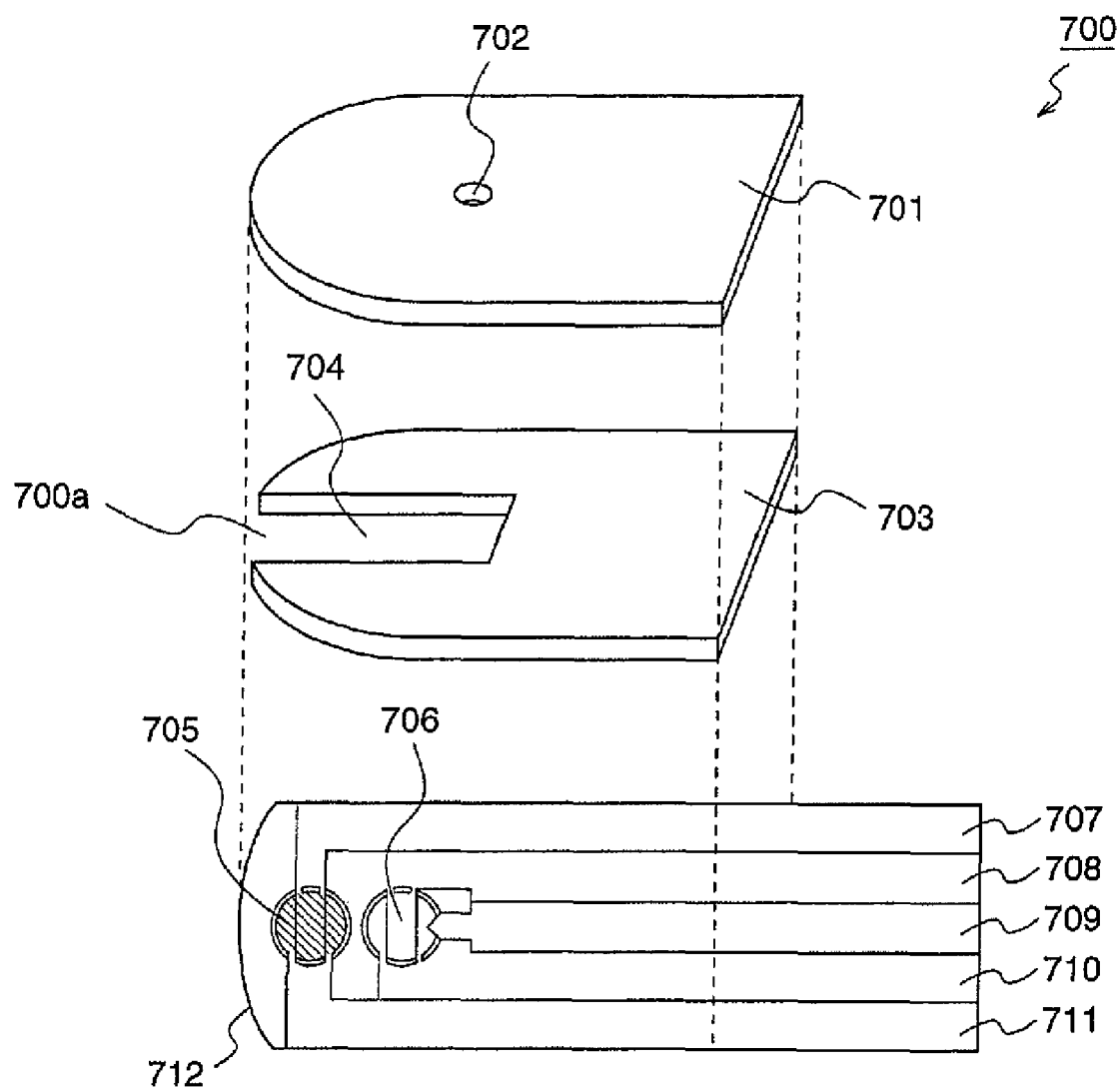
FIG. 8 is an exploded perspective view illustrating an example of configuration of the biosensor in the biosensor measurement system of the third embodiment.
Figure 9:
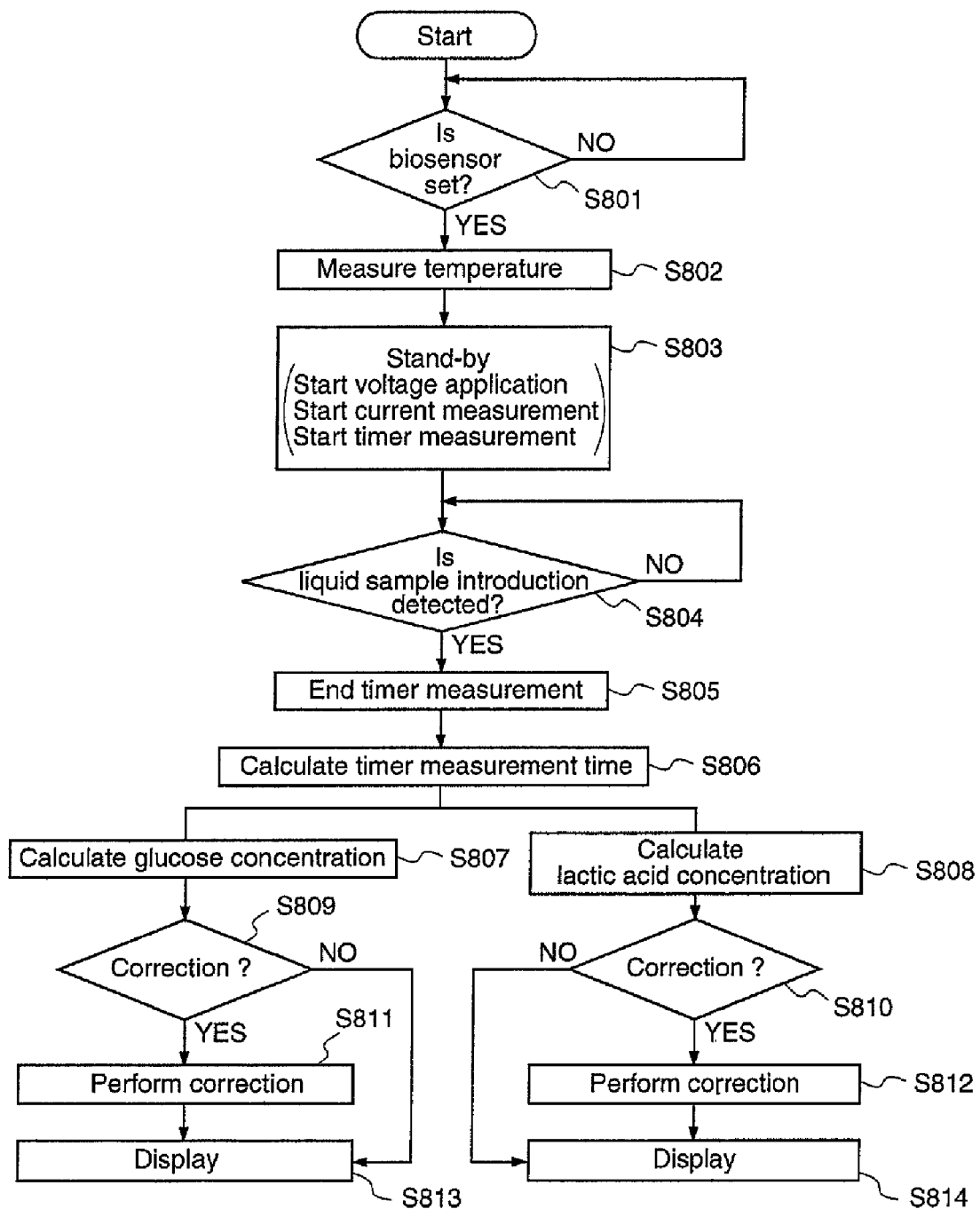
FIG. 9 is a diagram illustrating a liquid sample measurement method by the biosensor measurement system of the third embodiment.

As shown in FIG. 8, the biosensor 700 is obtained by laminating a cover 701 having an vent hole 702 in its center, a spacer 703 having an approximately rectangle-shaped sample supply channel 704 into which the liquid sample applied to a sample application part 700a is introduced, reagent layers 705 and 706, and an insulating substrate 712.

The reagent layer 705 supports a reagent which enzymatically reacts with lactic acid in the liquid sample. The reagent layer 706 supports a reagent which enzymatically reacts with glucose in the liquid sample. The insulating substrate 712 has an electrode layer on its surface, which electrode layer comprises the working electrode 707 for measuring lactic acid, the working electrode 708 for measuring glucose, the detection electrode 709, the counter electrode 710 for measuring glucose, and the counter electrode 711 for measuring lactic acid.

The biosensor 700 is different from the biosensor 30 in that the two types of reagent layers 705 and 706 for lactic acid measurement and glucose measurement are arranged, and lactic acid measurement is performed by the lactic acid measuring working electrode 707 and the lactic acid measuring counter electrode 711 while glucose measurement is performed by the glucose measuring working electrode 708 and the glucose measuring counter electrode 710, and analyte detections in the respective measurements are performed using the analyte detection electrode 709.

Hereinafter, the liquid sample measurement method by the biosensor measurement system 100b of this third embodiment will be described.

When the biosensor 700 is set in the support part of the measurement device 110b, whether the biosensor 700 is inserted or not is judged by the switch in the support part. When it is detected that the biosensor 700 is inserted, the power supply of the measurement device 110b is automatically turned on (step S801). Then, the ambient temperature is measured by the temperature sensor 120 (step S802), and the measurement device 110b goes into the analyte introduction stand-by state (step S803). The analyte introduction stand-by state is the state after starting voltage application from the reference voltage supply 119 to the connectors 123 to 127, starting current measurement by the current/voltage conversion circuit 116, and starting measurement of time from when the biosensor 700 is inserted to when the analyte is applied to the sensor 30 by the timer 122.

When blood as the analyte is applied to the biosensor 700, the current/voltage conversion circuit 116 reads a change in the current value to detect that the analyte is introduced (applied) into the sensor 700 (step S804). The count by the timer 122 is completed upon detecting the analyte introduction (step S805), and the time T from when the biosensor 700 is inserted in the measurement device 110b (the analyte introduction stand-by state) to when the analyte introduction is detected is calculated (step S806).

Then, the glucose concentration (step S807) and the lactic acid concentration (S808) in the blood that is applied to the biosensor 700 are calculated. At this time, correction amounts are obtained from the temperature correction tables stored in the RAM 121 on the basis of the ambient temperature measured in step S802, and corrections are performed for the measurement results of the glucose concentration and the lactic acid concentration in the blood that is applied to the biosensor 700. At this time, the corrections are desirably performed using a temperature correction table for correcting the glucose concentration and a temperature correction table for correcting the lactic acid concentration. This is because the influence of the ambient temperature differs depending on the measurement target substance.

Thereafter, whether or not corrections should be performed to the glucose concentration value calculated in step S807 and to the lactic acid concentration value calculated in step S808 are respectively judged on the basis of the time T calculated in step S806 (step S809, step S810). In these judgments, it is preferable to provide the judgmental standards for the glucose concentration measurement and the lactic acid concentration measurement, respectively. For example, the respective parameters are previously set within the same ranges as in the first embodiment for the glucose concentration measurement, while it is previously set that correction should be performed when the respective parameters are within the ranges described below for the lactic acid concentration measurement.

The time T is set so as to perform correction when it is within a range from 0.01 to 60 sec. Preferably, correction should be performed when time T is within a range from 0.01 to 30 sec, and more preferably, from 0.01 to 20 sec. The read interval of the time T is set to every 1 sec. Preferably, it is set to every 0.1 sec, and more preferably, every 0.01 sec.

The lactic acid concentration is set so as to perform correction when it is within a range from 5 to 300 mg/dl. Preferably, correction should be performed when the lactic acid concentration is within a range from 5 to 200 mg/dl, and more preferably, from 5 to 100 mg/dl.

The ambient temperature is set so as to perform correction when it is within a range from 5 to 45° C. Preferably, correction should be performed when the ambient temperature is within a range from 10 to 40° C., and more preferably, from 15 to 35° C.

When the analyte is blood, it is set to perform correction when the hematocrit value is within a range from 0 to 70%. Preferably, correction should be performed when the hematocrit value is within a range from 15 to 70%, and more preferably, from 30 to 70%. Calculation of the hematocrit value is desirably performed before calculation of the glucose concentration (process in step S807) and calculation of the lactic acid concentration (process in step S808), and more preferably, the glucose concentration and the lactic acid concentration should be corrected based on the calculated hematocrit value. Also in this case, the corrections are desirably performed using correction calibration curves for the glucose concentration and the lactic acid concentration, respectively, as in the case of the temperature correction table. This is because the degree of influence by the hematocrit value differs between the glucose concentration measurement and the lactic acid concentration measurement. Further, the hematocrit value is not necessarily measured by the biosensor 700, and for example, it may be previously calculated by a large-sized measurement apparatus and the calculated value may be input to the measurement device.

When it is judged in step S809 that correction should be performed, an amount of correction for the measurement result of the glucose concentration in the blood that is applied to the biosensor 700 is obtained from the correction table shown in FIG. 4 as in the first embodiment, and the measurement result is corrected (step S811). Further, when it is judged in step S810 that correction should be performed, an amount of correction for the measurement result of the lactic acid concentration in the blood is obtained from the correction table shown in FIG. 10, and the measurement result is corrected (step S812). The method of calculating the correction amount is identical to the method described in the first embodiment except that the correction table differs. In this way, most suitable corrections can be performed by using the correction tables which have been prepared for the glucose concentration measurement and the lactic acid concentration measurement, respectively. This is because the degree of influence by the fingertip heat differs between the glucose concentration measurement and the lactic acid concentration measurement.

The corrected values are displayed on the display part of the measurement device 110b as the concentrations of glucose and lactic acid included in the blood as the analyte (step S813, step S814). If it is judged from the time T that the reliability of the measurement result is unsatisfactory, an error display may be performed without displaying the measurement result, or it may be displayed that the reliability of the measurement result is low.

On the other hand, when it is judged in step S809 that correction is not necessary, the operation goes to step S813 to display the glucose concentration calculated in step S807 as it is. Further, when it is judged in step S810 that correction is not necessary, the operation goes to step S814 to display the lactic acid concentration calculated in step S808 as it is. In this third embodiment, it is judged that correction is not necessary when the time T exceeds 20 sec.

More reliable corrections can be realized by performing the above-described operations.

Figure 11A:
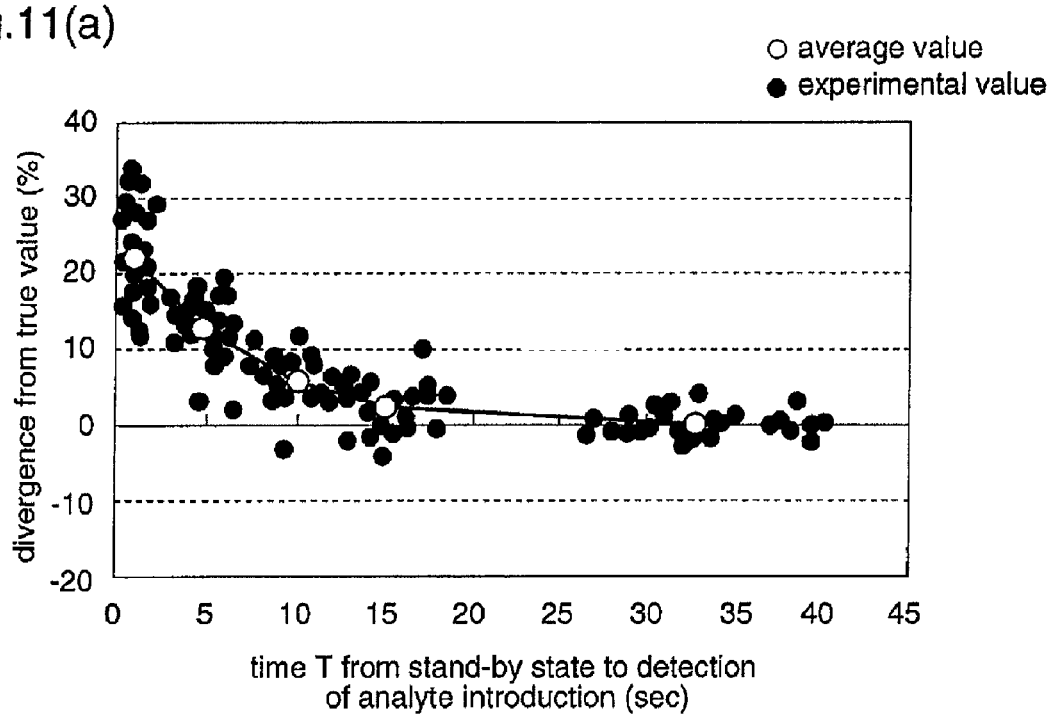
FIG. 11($a$) is a graph illustrating glucose response values obtained when the conventional biosensor measurement system is used, and FIG. 11($b$) is a graph illustrating the lactic acid response values obtained when the conventional biosensor measurement system is used.
Figure 11B:
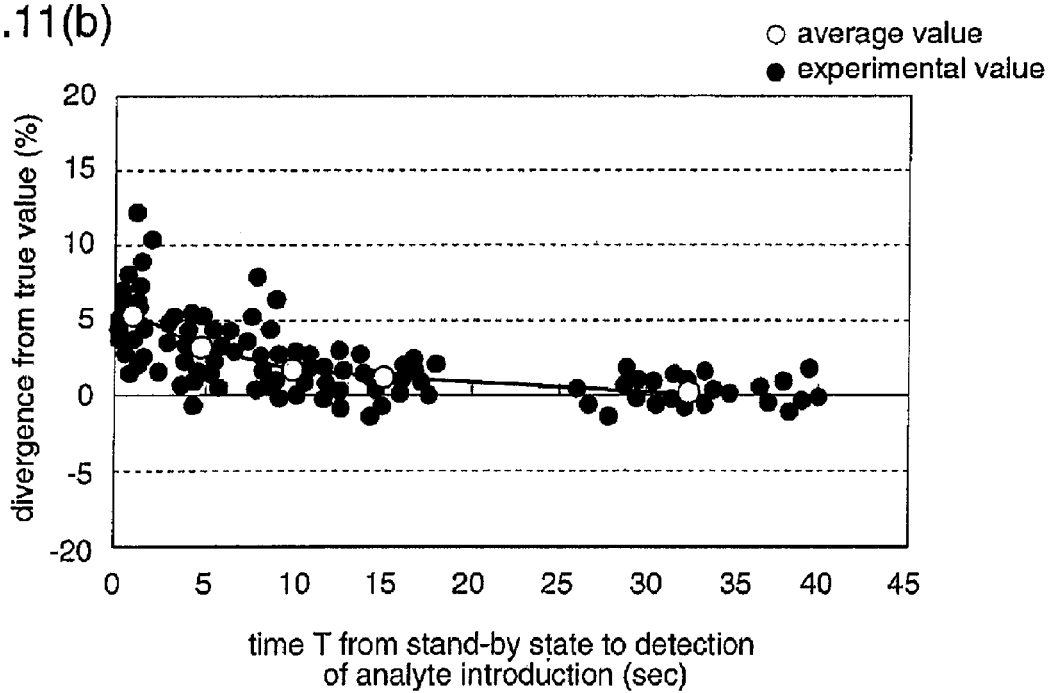

FIGS. 11(a) and 11(b) show the measurement result of the glucose concentration and the measurement result of the lactic acid concentration which are obtained by the conventional biosensor measurement system 20, respectively. The abscissa shows the time T(sec) from when the biosensor 30 is inserted in the measurement device 21 to when blood is applied to the sensor 30, and the ordinate shows the degree of divergence (%) from the true value. The measurement was performed at the ambient temperature of 25° C. using an analyte having a glucose concentration prepared at 85 mg/dl and a lactic acid concentration prepared at 50 mg/dl (hematocrit value of 45%). At this time, the biosensor 30 was inserted in the measurement device 21 by six donors having different fingertip temperatures, and the time T up to the application of the analyte after the insertion of the sensor 30 was measured within a range from 0.01 to 40 sec.

As can be seen from FIGS. 11(a) and 11(b), the degree of divergence from the true value becomes larger as the time T is shorter, and the degree of influence differs depending on the measurement target substance. That is, the fingertip heat influences the measurement result, and the influence by the heat differs depending on the measurement target substance.

On the other hand, in the biosensor measurement system 100b of this third embodiment, the measurement results of the glucose concentration and the lactic acid concentration in the blood that is applied to the biosensor 700 (these measurement results are values obtained after the temperature correction) are respectively corrected using the most suitable calibration curves on the basis of the time T from when the biosensor 700 is inserted in the measurement device 110b to when the blood is applied to the sensor 700.

Figure 12A:
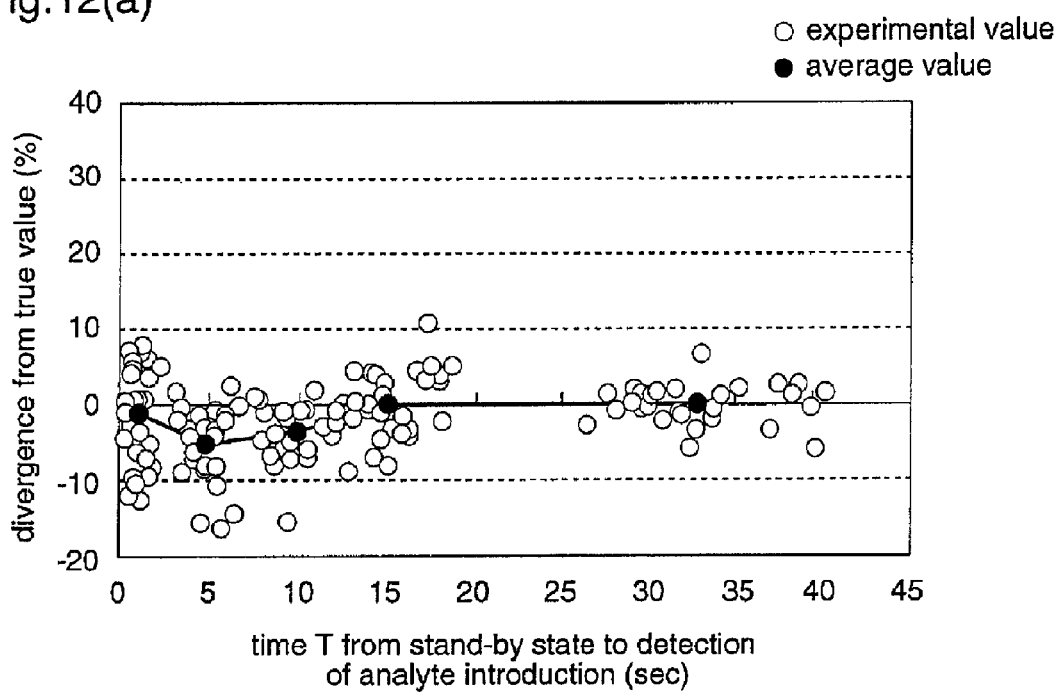
FIG. 12($a$) is a graph illustrating glucose response values obtained when the biosensor measurement system of the third embodiment is used, and FIG. 12($b$) is a graph illustrating the lactic acid response values obtained when the biosensor measurement system of the third embodiment is used.
Figure 12B:
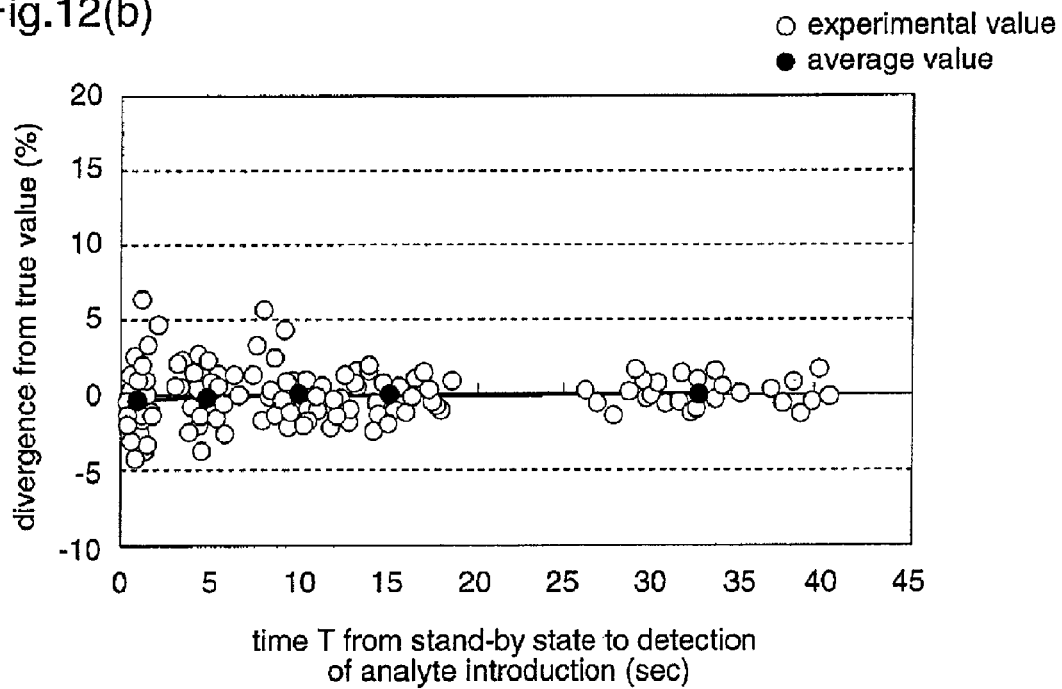

In this way, the measurement results of the glucose concentration and the lactic acid concentration in the blood that is applied to the biosensor 700 are respectively corrected based on the time T, and thereby the degree of divergence from the true value can be minimized even when the time T is within 20 sec as shown in FIGS. 12(a) and 12(b), resulting in improved measurement precision.

The numerical values on the correction tables shown in FIG. 10 are merely examples, and the correction amounts are not restricted thereto. Further, the number of tables is also not restricted to those shown in FIG. 10, and the measurement precision can be more improved as the number of tables becomes larger.

As described above, according to the liquid sample measurement method and apparatus of this third embodiment, the time T from when the biosensor 700 is inserted in the measurement device 110b to when blood is applied to the sensor 700 is measured, and the measurement results of the glucose concentration and lactic acid concentration in the blood that is applied to the biosensor 700 are corrected based on the measured time T, using the correction tables which are most suitable for the glucose concentration and the lactic acid concentration, respectively. Therefore, the influence of the fingertip heat on the measurement result is avoided, thereby obtaining a highly-precise measurement result even when the measurement time is short. Further, a highly-precise measurement apparatus can be realized at low cost without newly providing a temperature sensor for measuring the temperature of the biosensor 700 itself.

While in this third embodiment the biosensor 700 is an electrode type sensor, any measurement method can be similarly adopted so long as the measurement result is affected by the fingertip heat. For example, it may be an optical sensor, or a combination of an electrode type sensor and an optical sensor.

Further, while in this third embodiment the glucose concentration and the lactic acid concentration are described as plural measurement target substances to be measured in a single sensor, the measurement target substances are not restricted thereto. For example, various combinations such as glucose and cholesterol, glucose and triglyceride, glucose and hemoglobin A1c, glucose and ketone body, glucose and hematocrit, lactic acid and uric acid, uric acid and bilirubin are considered, and further, biological samples, ambient samples, food samples and the like can also be adopted with the same effects as described above. Further, the number of measurement target items is not restricted to two, and more than two items may be adopted.

Furthermore, while in this third embodiment plural measurement target substances are measured in a single biosensor, plural kinds of biosensors may be inserted to be used in a single measurement device. In this case, for example, the measurement device is made to recognize the kinds of the biosensors by electrode patterns of the biosensors or manual buttons of the measurement device, and correction tables most suitable for the respective biosensors are used, whereby most suitable corrections can be performed to the measurement items according to the respective types of biosensors, thereby obtaining highly precise measurement results as in the first to third embodiments.

It is to be noted that the present invention relates to a biosensor measurement system comprising a biosensor and a measurement device, and the biosensor is restricted to one which is directly held by the user and inserted in the measurement device to perform measurement, and therefore, a cartridge type biosensor is out of the scope of the invention.

APPLICABILITY IN INDUSTRY

A biosensor measurement system of the present invention can be utilized as a liquid sample measurement apparatus which is low in cost and has favorable measurement precision.

The invention claimed is:

1. A liquid sample measurement apparatus having a biosensor attached thereto, which measures the concentration of a specific component in a liquid sample that is applied to the biosensor, the liquid sample measurement apparatus including:
   a time measurement means for measuring the time from when the biosensor is attached to when the liquid sample is applied to the biosensor; and
   a measurement result correction means for correcting the measurement result of the concentration of the specific component in the liquid sample that is applied to the biosensor, on the basis of the time measured by the time measurement means.

2. A liquid sample measurement apparatus as defined in claim 1, wherein
   said measurement result correction means changes the amount of correction for the measurement result of the concentration of the specific component in the liquid sample that is applied to the biosensor, according to the time measured by the time measurement means.

3. A liquid sample measurement apparatus as defined in claim 2, wherein
   said measurement result correction means reduces the amount of correction when the time measured by the time measurement means is long.

4. A liquid sample measurement apparatus as defined in claim 1, wherein
   said measurement result correction means judges whether correction should be performed or not for the measurement result of the concentration of the specific component in the liquid sample that is applied to the biosensor, according to the time measured by the time measurement means.

5. A liquid sample measurement apparatus as defined in claim 4, wherein
   said measurement result correction means performs the correction when the time measured by the time measurement means is within a specific time.

6. A liquid sample measurement apparatus as defined in claim 1, wherein
   said measurement result correction means determines the amount of correction for the measurement result according to the measurement result of the concentration of the specific component in the liquid sample that is applied to the biosensor.

7. A liquid sample measurement apparatus as defined in claim 1 further including
   a temperature measurement part for measuring the ambient temperature at the measurement, and
   wherein said measurement result correction means determines the amount of correction for the measurement result of the concentration of the specific component in the liquid sample that is applied to the biosensor, according to the ambient temperature measured by the temperature measurement part.

8. A liquid sample measurement apparatus as defined in claim 1, wherein
   said measurement result correction means determines the amount of correction for the measurement result of the concentration of the specific component in the liquid sample that is applied to the biosensor, according to a second specific component which exists in the liquid sample and is different than the specific component.

9. A liquid sample measurement apparatus as defined in claim 8, wherein
   the liquid sample is blood, and
   the second specific component is the hematocrit value of the blood.

10. A liquid sample measurement apparatus as defined in claim 1, wherein
said measurement result correction means determines the amount of correction for the measurement result according to the type of the liquid sample that is applied to the biosensor.

11. A liquid sample measurement apparatus having a biosensor attached thereto, which measures the concentration of a specific component in a liquid sample that is applied to the biosensor, the liquid sample measurement apparatus including:
a time measurement means for measuring the time from when the biosensor is attached to when the liquid sample is applied to the biosensor;
a temperature sensor for measuring the ambient temperature at measurement;
a temperature correction means for correcting the ambient temperature measured by the temperature sensor, on the basis of the time measured by the time measurement means; and
a measurement result correction means for performing correction for the measurement result of the concentration of the specific component in the liquid sample that is applied to the biosensor, on the basis of the corrected ambient temperature.

* * * * *